United States Patent
Thompson

(10) Patent No.: US 6,495,540 B2
(45) Date of Patent: Dec. 17, 2002

(54) LACTAMS AS INHIBITORS OF A-β PROTEIN PRODUCTION

(75) Inventor: Lorin A. Thompson, Wilmington, DE (US)

(73) Assignee: Bristol - Myers Squibb Pharma Company

(*) Notice: Subject to any disclaimer, the term of this patent is extended or adjusted under 35 U.S.C. 154(b) by 0 days.

(21) Appl. No.: 09/817,957

(22) Filed: Mar. 27, 2001

(65) Prior Publication Data
US 2002/0010172 A1 Jan. 24, 2002

Related U.S. Application Data
(60) Provisional application No. 60/192,527, filed on Mar. 28, 2000.

(51) Int. Cl.⁷ .................. A61K 31/55; C07D 401/00; C07D 403/00; C07D 223/12; A61P 25/28
(52) U.S. Cl. ................. 514/212.03; 514/212.08; 540/524; 540/525; 540/527
(58) Field of Search ................. 540/524, 525, 540/527; 514/212.03, 212.08

(56) References Cited

U.S. PATENT DOCUMENTS

| | | |
|---|---|---|
| 5,283,241 A | 2/1994 | Bochis et al. |
| 5,602,145 A | 2/1997 | Samanen |
| 5,672,596 A | 9/1997 | Wyvratt et al. |
| 5,710,153 A | 1/1998 | Ohmoto et al. |
| 5,710,171 A | 1/1998 | Dinsmore et al. |
| 5,756,528 A | 5/1998 | Anthony et al. |
| 5,763,437 A | 6/1998 | Sato et al. |
| 5,852,010 A | 12/1998 | Graham et al. |
| 5,856,326 A | 1/1999 | Anthony et al. |
| 5,859,012 A | 1/1999 | Dinsmore et al. |
| 5,869,682 A | 2/1999 | DeSolms |
| 5,872,135 A | 2/1999 | DeSolms |
| 5,885,995 A | 3/1999 | Dinsmore |
| 5,891,889 A | 4/1999 | Anthony et al. |
| 5,905,077 A | 5/1999 | Jungheim et al. |
| 5,919,785 A | 7/1999 | Dinsmore et al. |
| 5,965,578 A | 10/1999 | Graham et al. |

FOREIGN PATENT DOCUMENTS

| | | |
|---|---|---|
| DE | 2934355 | 3/1981 |
| EP | 0842944 | 5/1998 |
| WO | 9217460 | 10/1992 |
| WO | 9405634 | 3/1994 |
| WO | 9617833 | 5/1996 |
| WO | 9617833 | 6/1996 |
| WO | 9618602 | 6/1996 |
| WO | 9620918 | 7/1996 |
| WO | 963165 | 10/1996 |
| WO | 9639137 | 12/1996 |
| WO | 9719053 | 5/1997 |
| WO | 09727852 | 8/1997 |
| WO | 9736900 | 10/1997 |
| WO | 9738664 | 10/1997 |
| WO | 9745412 | 12/1997 |
| WO | 9816523 | 4/1998 |
| WO | 9827053 | 6/1998 |
| WO | WO 98/28268 | * 7/1998 |
| WO | 9828268 | 7/1998 |
| WO | 9837079 | 8/1998 |
| WO | 9841510 | 9/1998 |
| WO | 9844797 | 10/1998 |
| WO | 9858915 | 12/1998 |
| WO | 9900654 | 1/1999 |
| WO | 9903826 | 1/1999 |
| WO | 9907731 | 2/1999 |
| WO | 9917777 | 4/1999 |
| WO | 9919305 | 4/1999 |
| WO | 9967221 | 12/1999 |
| WO | 0007995 | 2/2000 |

* cited by examiner

*Primary Examiner*—Bruck Kifle

(57) ABSTRACT

This invention relates to novel lactams having the Formula (I):

(I)

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

18 Claims, No Drawings

LACTAMS AS INHIBITORS OF A-β PROTEIN PRODUCTION

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND ACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, *Annu Rev Cell Biol,* 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885–890). The isolation and sequence data for the first 28 amino acids are described in U.S. Pat. No 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

As evidenced by the interest in the treatment of neurological disorders related to β-amyloid production, such as Alzheimer's disease and Down's Syndrome, a wide variety of compounds which inhibit Aβ protein production have been studied. For example, PCT publication number WO 98/28268 describes compounds of the general formula:

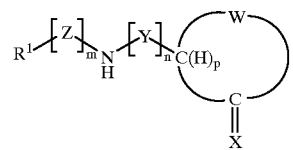

as inhibitors of β-amyloid peptide release and having utility in treating Alzheimer's disease. Though some of the present compounds of this invention appear to fall within the generic description of the above publication, they are not specifically disclosed, suggested, or claimed therein.

Thus, it is desirable to develop additional inhibitors of Aβ protein production to treat Alzheimer's disease or Down's syndrome. The present invention discloses compounds of enhanced activity in inhibiting Aβ protein production.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

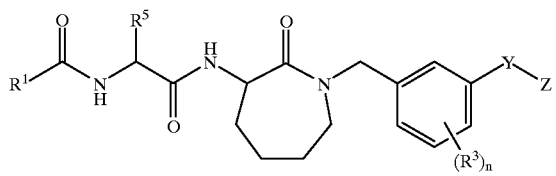

(I)

or pharmaceutically acceptable salt or prodrug forms thereof, wherein $R^1$, $R^2$, $R^3$, n, Y and Z are defined below, are effective inhibitors of the Aβ protein-production.

DETAILED DESCRIPTION OF PREFERRED EMBODIMENTS

[1] In a first embodiment, the present invention provides a novel compound of Formula (I):

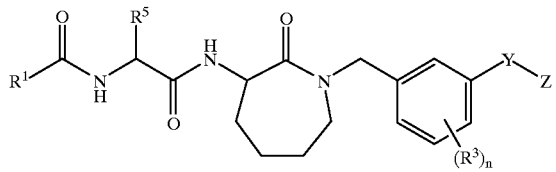

(I)

or a pharmaceutically acceptable salt or prodrug thereof, wherein:

$R^1$ is $C_1$–$C_6$ alkyl substituted with 0–3 $R^{1a}$; $C_6$–$C_{10}$ aryl substituted with 0–3 $R^{1b}$; $C_3$–$C_6$ cycloalkyl substituted with 0–3 $R^{1b}$; or 5 to 10 membered heterocycle substituted with 0–3 $R^{1b}$;

$R^{1a}$, at each occurrence, is independently selected from: H, $CF_3$, $OR^{14}$, Cl, F, Br, I, =O, CN, $NO_2$, $NR^{15}R^{16}$; $C_3$–$C_{10}$ carbocycle substituted with 0–3 $R^{1b}$; $C_6$–$C_{10}$ aryl substituted with 0–3 $R^{1b}$; and 5 to 10 membered heterocycle substituted with 0–3 $R^{1b}$;

$R^{1b}$, at each occurrence, is independently selected from H, OH, $C_1$–$C_4$ alkyl, $C_1$–$C_4$ alkoxy, Cl, F, Br, I, CN, $N_3$, $NO_2$, $NR^{15}R^{16}$, phenoxy, $C_1$–$C_4$ thioalkoxy and $CF_3$;

$R^5$ is $C_1$–$C_4$ alkyl, cyclopropyl, cyclopropylmethyl, cyclopropylethyl, cyclobutyl, cyclobutylmethyl, or cyclobutylethyl;

$R^3$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

n is 0, 1, 2, or 3;

Y is a bond, —C(=O)—, —O—, —S—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;

Z is $C_1$–$C_3$ alkyl substituted with 0–2 $R^{12}$; $C_6$–$C_{10}$ aryl substituted with 0–4 $R^{12b}$; $C_3$–$C_{10}$ carbocycle substituted with 0–2 $R^{12}$; or $C_5$–$C_{10}$ membered heterocycle substituted with 0–4 $R_{12b}$;

$R^{12}$ is $C_6$–$C_{10}$ aryl substituted with 0–4 $R_{12b}$; or $C_3$–$C_{10}$ carbocycle substituted with 0–2 $R^{12}$;

$R^{12b}$, at each occurrence, is independently selected from H, OH, $C_1$–$C_6$ alkyl, $C_1$–$C_6$ thioalkyl, $C_1$–$C_4$ alkoxy, $C_1$–$C_4$ haloalkoxy, $C_1$–$C_4$ haloalkyl, Cl, F, Br, I, CN, $NO_2$, $NR^{15}R^{16}$, and $CF_3$;

$R^{14}$ is H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, benzyl, phenethyl, —C(=O)—($C_1$–$C_6$ alkyl) and —S(=O)$_2$—($C_1$–$C_6$ alkyl);

$R^{19}$, at each occurrence, is independently selected from H, OH, $C_1$–$C_6$ alkyl, phenyl, benzyl, phenethyl, —C(=O)—($C_1$–$C_6$ alkyl), and —S(=O)$_2$—($C_1$–$C_6$ alkyl); and $R^{19b}$ is H, $C_1$–$C_6$ alkyl, $C_3$–$C_8$ cycloalkyl, phenyl, benzyl or phenethyl.

[2] In a more preferred embodiment, the present invention provides for a compound of Formula I,

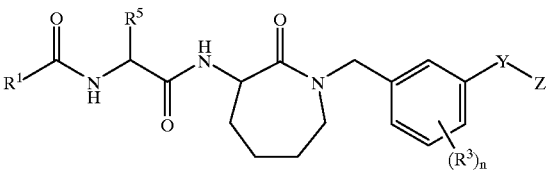

(I)

or a pharmaceutically acceptable salt or prodrug thereof, wherein:

$R^1$ is $C_1$–$C_6$ alkyl substituted with 0–1 $R^{1a}$; $C_3$–$C_6$ cycloalkyl substituted with 0–1 $R^{1b}$; phenyl substituted with 0–2 $R^{1b}$; naphthyl substituted with 0–2 $R^{1b}$; or pyridyl substituted with 0–2 $R^{1b}$;

$R^{1a}$, at each occurrence, is independently selected from: H, $CF_3$, $OR^{14}$, Cl, F, Br, I; $C_3$–$C_{10}$ carbocycle substituted with 0–3 $R^{1b}$; and $C_6$–$C_{10}$ aryl substituted with 0–3 $R^{1b}$;

$R^{1b}$, at each occurrence, is independently selected from H, OH, methyl, ethyl, propyl, butyl, methoxy, ethoxy, propoxy, butoxy, Cl, F, Br, I, CN, $NO_2$, $N_3$, $SCH_3$, $NR^{15}R^{16}$, phenoxy, and $CF_3$;

$R^5$ is methyl, ethyl, propyl, isopropyl, butyl, isobutyl, cyclopropylmethyl, or cyclobutylmethyl;

$R^3$, at each occurrence, is independently selected from H, OH, methyl, ethyl, propyl, butyl, methoxy, ethoxy, propoxy, butoxy, Cl, F, Br, I, CN, $NO_2$, and $CF_3$;

n is 0, 1, or 2;

Y is a bond, —C(=O)—, —O—, —S—, —C(=O)O—, or —OC(=O)—;

Z is $C_1$–$C_3$ alkyl substituted with 0–2 $R^{12}$; or $C_6$–$C_{10}$ aryl substituted with 0–4 $R^{12b}$;

$R^{12}$ is $C_6$–$C_{10}$ aryl substituted with 0–4 $R^{12b}$; or $C_3$–$C_6$ carbocycle substituted with 0–4 $R^{12b}$;

$R^{12b}$, at each occurrence, is independently selected from H, OH, $C_1$–$C_4$ alkyl, $C_1$–$C_4$ alkoxy, Cl, F, Br, I, CN, $NO_2$, $SCH_3$, $NR^{15}R^{16}$, and $CF_3$;

$R^{14}$ is H, phenyl, benzyl, or $C_1$–$C_6$ alkyl;

$R^{15}$, at each occurrence, is independently selected from H, $C_1$–$C_4$ alkyl, benzyl, and phenethyl; and $R^{16}$, at each occurrence, is independently selected from H, $C_1$–$C_4$ alkyl, benzyl, and phenethyl.

[3] In an even more preferred embodiment, the present invention provides for a compound of Formula I,

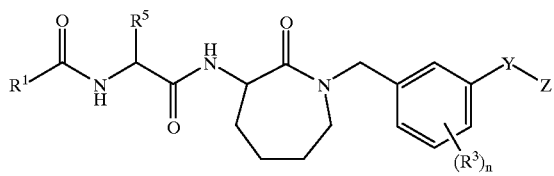

(I)

or a pharmaceutically acceptable salt or prodrug thereof, wherein:

$R^1$ is methyl, ethyl, propyl, butyl, pentyl, hexyl, cyclopropyl, cyclobutyl, cyclopentyl, cyclohexyl, naphthyl, pyridyl; methyl substituted with 1 $R^{1a}$; ethyl substituted with 1 $R^{1a}$; or phenyl substituted with 1–3 $R^{1b}$;

$R^{1a}$, at each occurrence, is independently selected from: H, $CF_3$, $OR^{14}$, Cl, F, Br, I; $C_3$–$C_6$ cycloalkyl substituted with 0–3 $R^{1b}$; and phenyl substituted with 0–3 $R^{1b}$;

$R^{1b}$, at each occurrence, is independently selected from H, OH, methyl, ethyl, propyl, butyl, methoxy, ethoxy, propoxy, butoxy, Cl, F, Br, I, CN, $NO_2$, $N_3$, $SCH_3$, $NR^{15}R^{16}$, phenoxy, and $CF_3$;

$R^5$ is methyl;

$R^3$, at each occurrence, is independently selected from H, OH, methyl, ethyl, methoxy, ethoxy, Cl, F, Br, I, CN, $NO_2$, and $CF_3$;

n is 0 or 1;

Y is a bond or —O—;

Z is $C_1$–$C_3$ alkyl substituted with 0–2 $R^{12}$; or phenyl substituted with 0–3 $R^{12b}$;

$R^{12}$ is $C_3$–$C_6$ cycloalkyl substituted with 0–3 $R^{12b}$; phenyl substituted with 0–3 $R^{12b}$;

$R^{12b}$, at each occurrence, is independently selected from H, OH, methyl, ethyl, propyl, butyl, methoxy, ethoxy, propoxy, butoxy, $SCH_3$, $C_1$–$C_2$ haloalkyl, $C_1$–$C_2$ haloalkoxy, Cl, F, Br, I, CN, $NO_2$, $NR^{15}R^{16}$, and $CF_3$;

$R^{14}$ is H, methyl, ethyl, phenyl, or benzyl;

$R^{15}$, at each occurrence, is independently selected from H, methyl, ethyl, propyl, butyl, benzyl, and phenethyl; and $R^{16}$, at each occurrence, is independently selected from H, methyl, ethyl, propyl, butyl, benzyl, and phenethyl.

[4] In another embodiment, the present invention provides for a compound of Formula (Ia),

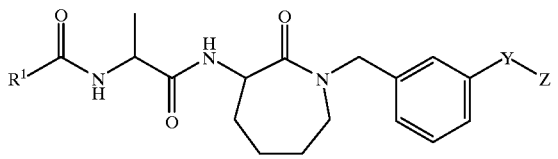

(Ia)

or a pharmaceutically acceptable salt or prodrug thereof, wherein:

$R^1$ is methyl substituted with 1 $R^{1a}$; ethyl substituted with 1 $R^{1a}$; phenyl substituted with 1–3 $R^{1b}$; methyl, ethyl, propyl, butyl, pentyl, hexyl, cyclopropyl, cyclobutyl, cyclopentyl, cyclohexyl, naphthyl, or pyridyl;

$R^{1a}$ is phenyl substituted with 0–3 $R^{1b}$; cyclopropyl substituted with 0–1 $R^{1b}$; cyclobutyl substituted with 0–1 $R^{1b}$; cyclopentyl substituted with 0–1 $R^{1b}$; or cyclohexyl substituted with 0–1 $R^{1b}$;

$R^{1b}$, at each occurrence, is independently selected from H, OH, methyl, ethyl, propyl, butyl, methoxy, ethoxy, propoxy, butoxy, Cl, F, Br, I, CN, $NO_2$, $N_3$, $SCH_3$, phenoxy, and $CF_3$;

Z is methyl substituted with $R^{12}$; or phenyl substituted with 0–2 $R^{12b}$;

$R^{12}$ is phenyl substituted with 0–2 $R^{12b}$;

$R^{12b}$, at each occurrence, is independently selected from H, OH, methyl, ethyl, methoxy, ethoxy, Cl, F, Br, I, CN, $NO_2$, $SCH_3$, $NR^{15}R^{16}$, $OCF_3$, and $CF_3$;

$R^{15}$, at each occurrence, is independently selected from H, methyl, and ethyl; and $R^{16}$, at each occurrence, is independently selected from H, methyl, and ethyl.

[5] In an even more preferred embodiment, the present invention provides for a compound Formula (Ib);

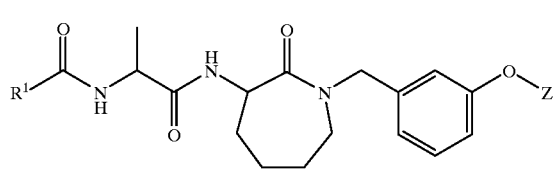

(Ib)

or a pharmaceutically acceptable salt or prodrug thereof, wherein:

$R^1$ is methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$cyclohexyl, —CH$_2$CH$_2$cyclopentyl, phenylmethyl, 2-chlorophenylmethyl, 2-fluorophenylmethyl, 2-bromophenylmethyl, 2-hydroxyphenylmethyl, 2-nitrophenylmethyl, 2-methylphenylmethyl, 2-methoxyphenylmethyl, 2-phenoxyphenylmethyl, 2-trifluoromethylphenylmethyl, 3-hydroxyphenylmethyl, 3-nitrophenylmethyl, 3-fluorophenylmethyl, 3-chlorophenylmethyl, 3-bromophenylmethyl, 3-thiomethoxyphenylmethyl, 3-methylphenylmethyl, 3-trifluoromethylphenylmethyl, 3-methoxyphenylmethyl, 4-chlorophenylmethyl, 4-bromophenylmethyl, 4-nitrophenylmethyl 4-methylphenylmethyl, 4-hydroxyphenylmethyl, 4-methoxyphenylmethyl, 4-ethoxyphenylmethyl, 4-butoxyphenylmethyl, 4-iso-propylphenylmethyl, 4-trifluoromethylphenylmethyl, 4-azidophenylmethyl, 4-cyanophenylmethyl,4-ethylphenylmethyl, 4-fluorophenylmethyl, 4-iodophenylmethyl, 2,3-dichlorophenylmethyl, 2,5-difluorophenyl, 2,3-difluorophenylmethyl, 2,4-dichlorophenylmethyl, 2,5-dimethoxyphenylmethyl, 3,4-dichlorophenylmethyl, 3,4-difluorophenylmethyl, 3,4-dimethoxyphenylmethyl, 3,5-difluorophenylmethyl, 3,5-dichlorophenylmethyl, 3,5-di-(trifluoromethyl)phenylmethyl, 3,5-dimethoxyphenylmethyl, 2,4-difluorophenylmethyl, 2,6-difluorophenylmethyl, 2,5-difluorophenylmethyl, 2-fluoro-3-trifluoromethylphenylmethyl, 4-fluoro-2-trifluoromethylphenylmethyl, 2-fluoro-4-trifluoromethyl-phenylmethyl, 2-choro-6-fluorophenylmethyl, 2-fluoro-6-chlorophenylmethyl, 2,5-dimethylphenylmethyl, 2-fluoro-3-trifluoromethylphenylmethyl, 3-(trifluoromethyl)-(4-chloro-phenylmethyl, 3-chloro-4-cyano-phenylmethyl, 3-chloro-4-iodo-phenylmethyl, 3,4,5-trichlorophenylmethyl, 3,4,5-trifluorophenylmethyl, 3,4,5-trimethoxyphenylmethyl, 3,4,5-tri(trifluoromethyl) phenylmethyl, 2,4,6-trifluorophenylmethyl, 2,4,6-trimethylphenylmethyl, 2,4,6-tri-(trifluoromethyl) phenylmethyl, 2,3,5-trifluorophenylmethyl, 2,4,5-trifluorophenylmethyl, 2-phenylethyl, 2-(4-nitrophenyl) ethyl, 2-(4-methoxyphenyl)ethyl, (1-phenyl)ethyl, 1-(p-chorophenyl)ethyl, (1-trifluoromethyl)phenylethyl, (4-methoxyphenyl)ethyl, 1-naphthyl, 2-naphthyl, pyrid-2-yl, pyrid-3-yl, or pyrid-4-yl; and Z is is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, or 4-CF$_3$O-phenyl.

[6] In another more preferred embodiment the present invention provides for a compound of Formula (I) which is

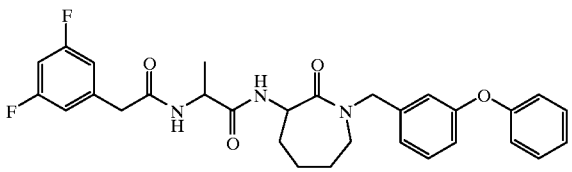

or a pharmaceutically acceptable salt or prodrug thereof.

[7] In a second embodiment the present invention provides for pharmaceutical composition comprising a compound of Formula (I) and a pharmaceutically acceptable carrier.

[8] In a third embodiment the present invention provides for a method for the treatment of neurological disorders associated with β-amyloid production comprising administering to a host in need of such treatment a therapeutically effective amount of a compound of Formula (I).

[9] In a fifth embodiment the present invention provides for a method for inhibiting γ-secretase activity comprising administering to a host in need of such inhibition a therapeutically effective amount of a compound of Formula (I) that inhibits γ-secretase activity.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No 4,666,829. The 43 amino acid sequence is:

```
 1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is an keto (i.e. =O), then 2 hydrogens on the atom are replaced.

When any variable (e.g. R$^{12}$) occurs more than one time in any constituent or formula for a compound, its definition at each occurrence is independent of its definition at every other occurrence. Thus, for example, if a group is shown to be substituted with 0–2 R$^{12}$, then said group may optionally be substituted with up to two R$^{12}$ groups and R$^{12}$ at each occurrence is selected independently from the definition of R$^{12}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "C$_1$–C$_6$ alkyl", denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon-carbon bonds which may occur in any stable point along the chain. Examples of "C2–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, or $C_1$–$C_4$ haloalkyl.

The compounds herein described may have asymmetric centers. One enantiomer of a compound of Formula (I) may display superior biological activity over the opposite enantiomer. For example carbon 3 of lactam ring of Formula (I') may exist in either an S or R configuration. Thus, for example, both R or S configurations at carbon 3 in Formula (I'-3R) and (I'-3S) are considered part of the invention. Examples of such configuration include, but are not limited to,

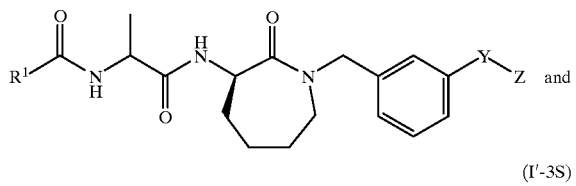
(I'-3R) and

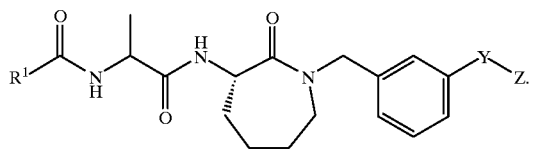
(I'-3S)

The (S)—configuration at carbon 3 of the lactam ring is preferred.

When required, separation of the racemic material can be achieved by methods known in the art. Additionally, the carbon atom to which $R^5$ is attached may display superior biological activity over the opposite enantiomer. For example, when $R^5$ is $C_1$–$C_4$ alkyl, the configuration of the carbon may be described as R or S. All configurations are considered part of the invention; however, the S configuration of the carbon bearing $R^5$ is more preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and acetamide, formamide and benzamide derivatives of amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A variety of compounds of Formula (I) can be prepared by methods described in Scheme 1. The protected α-amine 2 of the α-amino-ε-caprolactam 1 can be prepared by methods well known in the literature for amino protecting groups as discussed in Theodora W. Greene's book "Protective Groups in Organic Synthesis", like N-Boc using di-t-butyldicarbonate in an appropriate solvent like DMSO. The lactam nitrogen of compound 2 can be alkylated to give compound 3 by generating the anion with bases such as LDA, lithium bis(trimethylsilyl)amide or sodium hydride in solvents like THF, with or without co-solvents such as DMPU or HMPA and reacting this with a variety of groups, each of which containing a leaving groups (LG) such as a bromide, iodide, mesylate or tosylate. Alkylating agents such as α-bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304–305, 342–347, 695–698.

Scheme 1

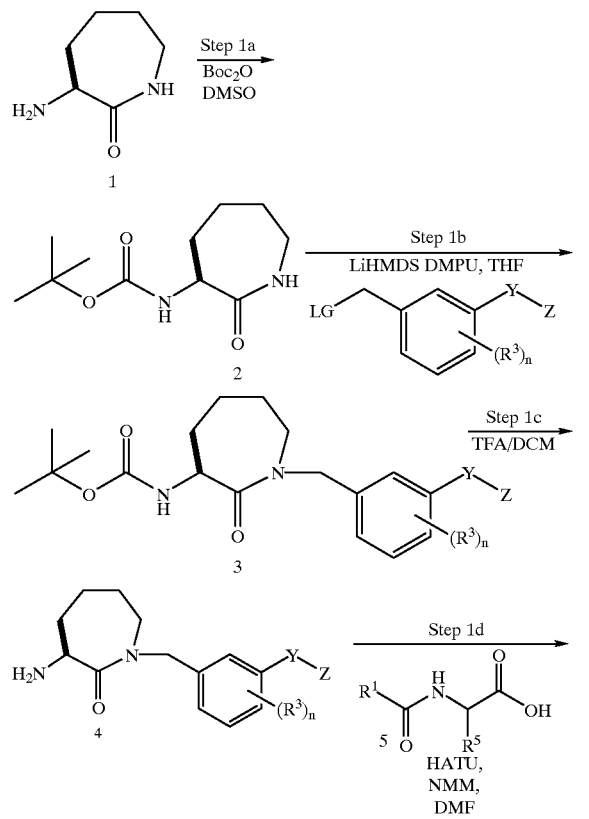

-continued

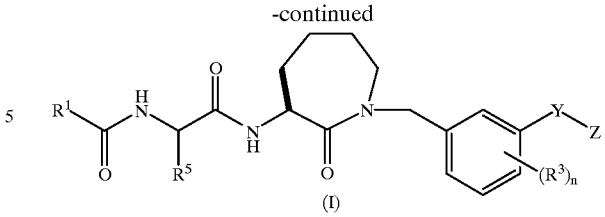

The N-Boc protecting group of compound 3 can be removed by any number of methods well known in the literature like TFA in methylene chloride to give an amine 4. The amine 4 can be coupled to an appropriately substituted carboxylic acid 5 or acid chloride by methods well described in the literature for making amide bonds, like TBTU in DMF with a base like NMM to give an elaborated compound of Formula (I).

Appropriate carboxylic acid 5 is available through the chemistry shown in Scheme 2. Thus, coupling of an amino acid ester 5b under standard conditions including Schotten-Bowman conditions produces an amide 5a. The carboxylic acid 5 is available through saponification of the ester 5a under standard basic conditions. Alternatively, the amide 5a can be formed using the amino acid ester 5b and a carboxylic acid using any of the standard coupling agents mentioned above or known to one skilled in the art.

Scheme 2

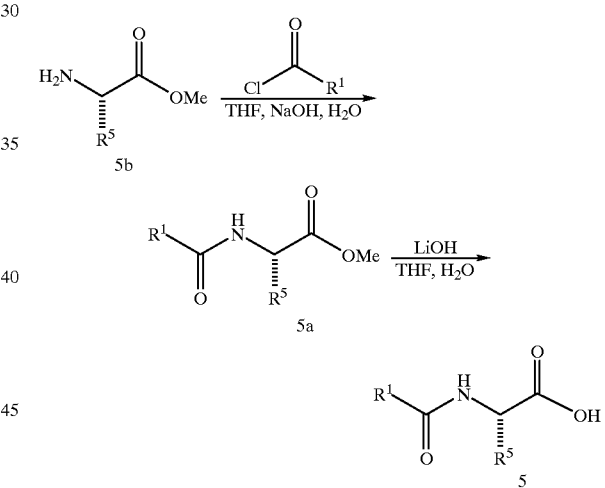

Methods for the synthesis of lactams and alkylation of lactams are known in the art and are disclosed in a number of references including PCT publication number WO 98/28268 (published Jul. 2, 1998) and PCT publication number WO 00/07995 (published Feb. 17, 2000), which are hereby incorporated in their entirety by reference.

Experimental

Chemical abbreviations used in the Examples are defined as follows: "DMPU" for 1,3-dimethyl-3,4,5,6-tetrahydro-2 (1H)-pyrimidone, "TBTU" for O-(1H-benzotriazol-1-yl)-N,N,N',N'-tetramethyluronium tetrafluoroborate, "HATU" for O-(7-azabenzotriazol-1-yl)-N,N,N',N'-tetrmethyluronium hexafluorophosphate, "TFA" for trifluoroacetic acid, "NMM" for n-methylmorpholine, and "BOP" for benzotriazol-1-yloxytris-(dimethylamino-phosphonium hexafluorophosphate. "HPLC" is an abbreviation used herein for high pressure liquid chromatography.

Using conditions generally known to one skilled in the art, compounds of the present invention are generally purified by HPLC. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable.

EXAMPLE 1

((2S)-2-[2-(3,5-Difluorophenyl)-acetylamino]-N-[(3S)-2-oxo-1-(3-phenoxy-benzyl)-azepan-3-yl]-propionamide)

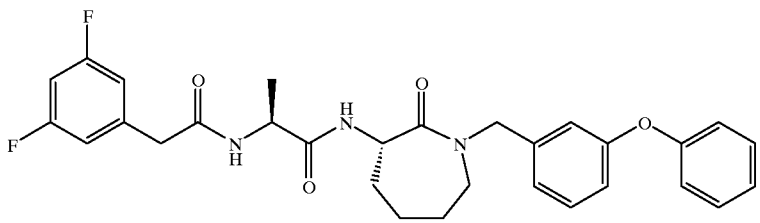

Step 1a: Di-tert-butyldicarbonate (10.2 g, 46.7 mmoles) was added portion wise to a solution of L-(−)-α-amino-ε-caprolactam 1 (5.0 g, 39.0 mmoles) in dimethyl sulfoxide (30 mL). After 5 h at rt, the reaction was partitioned between water (100 mL) and ethyl acetate. The combined organic extracts were washed successively with 1 M HCl (50 mL), brine, and dried (MgSO$_4$) and concentrated in vacuo. The residue was recrystallized in 1:1 v/v ether-hexanes, 2 crops yielded the desired caprolactam 2 (Scheme 1) as a white solid (6.26 g, 70%). MS(M+H-BOC)$^+$129.

Step 1b: A 1 M solution of lithium bis(trimethylsilyl)amide was added dropwise to a solution of caprolactam 2 (0.3 g, 1.31 mmoles) in tetrahydrofuran (5 mL) at −78° C. After 30 minutes a solution of m-phenoxybenzyl bromide (0.43 g, 1.63 mmoles) in tetrahydrofuran (4 mL) was added to the mixture dropwise. The reaction was allowed to come to ambient temperature, stirred for 16 h, then partitioned between water and ethyl acetate. The combined organic extracts were washed successively with water (20 mL), brine (20 mL), dried (MgSO$_4$) and concentrated in vacuo. The crude residue was purified by silica gel chromatography (ethyl acetate:hexanes, 5:95 then ethyl acetate:hexanes, 15:85) to give the desired caprolactam 3 (Scheme 1, R$^3$ is H, Y—Z is phenoxy) (360 mg, 67%) as a clear oil. MS(M-Ot-Bu)$^+$=337.

m-Phenoxybenzyl bromide. Triphenylphosphine (3.40 g, 13.0 mmoles) and carbontetrabromide (4.20 g, 13.0 mmoles) were added successively to a solution of m-phenoxybenzyl alcohol (1.5 mL, 8.6 mmoles). After 4 h at rt the mixture was concentrated and was purified by silica gel column (hexanes, then ethyl acetate:hexanes, 5:95) to give the desired bromide (1.3 g, 57%) as a yellow oil. MS(M−Br)$^+$=183.

Step 1c: Trifluoroacetic acid (5 mL) was added to a solution of 3 in dichloromethane (15 mL). After 3 h at rt the solution was concentrated in vacuo. The residual trifluoroacetic acid was removed from residue by azeotrope with toluene (50 mL) then dichloromethane (30 mL) to yield the desired caprolactam 4 (390 mg, 99%) as a clear oil. MS (M+H)$^+$=311.

Step 1d: (2S)-2-[2-(3,5-Difluoro-phenyl)-acetylamino]-propionic acid (74 mg, 0.30 mmol, prepared according to the chemistry described in Scheme 2 where R$^5$ is CH$_3$ and R$^1$ is —CH$_2$-3,5-difluoro-phenyl) was dissolved in 1.5 mL of DMF and treated with HATU (116 mg, 0.30 mmol) and N-methylmorpholine (110 μL, 0.9 mmol). After 5 min, the DMF solution was transferred by pipet into a flask containing 115 mg (0.37 mmol) of the caprolactam 4. After the reaction solution was stirred for 16 h at rt, the solution was diluted with 10 mL each of ethyl acetate and 1 N HCl. The organic layer was separated and washed sequentially with 5 mL of 1 N HCl (2×), a saturated NaHCO$_3$ solution (1×5 mL) and brine (1×5 mL). The organic layer was then dried and concentrated; and the residue was purified by chromatography eluting with 4:1 ethyl acetate/hexanes to provide the title compound, Example 1, as a white powder. MS(ESI) (M+H)$^+$=536.

Utility

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γ secretase activity, either directly or indirectly, control the production of Aβ. Such inhibition of β or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including J. Med. Chem. 1999, 42, 3889–3898, PCT publication number WO 98/22493, EPO publication number 0652009, U.S. Pat. No. 5,703,129 and U.S. Pat. No. 5,593,846; all hereby incorporated by reference.

The compounds of the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compound of the present invention is demonstrated using assays for such activity, for example, using the assay described below. The compound of the present invention has been shown to inhibit the activity of γ-secretase, as determined by the Aβ immunoprecipitation assay.

A compound provided by this invention should also be useful as a standard and reagent in determining the ability of a potential pharmaceutical to inhibit Aβ production. These would be provided in commercial kits comprising a compound of this invention.

As used herein "μg" denotes microgram, "mg" denotes milligram, "g" denotes gram, "μL" denotes microliter, "mL"

denotes milliliter, "L" denotes liter, "nM" denotes nanomolar, "µM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetic acid.

A compound is considered to be active if it has an $IC_{50}$ or $K_i$ value of less than about 100 µM for the inhibition of Aβ production. Preferrably the $IC_{50}$ or $K_i$ value is less than about 10 µM; more preferrably the $IC_{50}$ or $K_i$ value is less than about 0.1 µM. The present invention has been shown to inhibit Aβ protein production with an $IC_{50}$ or $K_i$ value of less than 100 µM.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1× Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 µl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 µl protein A Sepharose. After incubation overnight at 40° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an $IC_{50}$ less than 100 µM.

C-Terminus β Amyloid Precursor Protein Accumulation Assay

The effect of a test compound on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% $NaN_3$). Again, lysates are precleared with 5 ul normal rabbit serum/ 50 ul protein A Sepharose, followed by the addition of BC-1 antiserum (15 µl;) and 50 µl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an $IC_{50}$ less than 100 µM.

Aβ Immunoprecipitation Assay

This immunoprecipitation assay is specific for γ-secretase (i.e., proteolytic activity required to generate the C-terminal end of Aβ either by direct cleavage or generating a C-terminal extended species which is subsequently further proteolyzed). N 9 cells are pulse labeled in the presence of a reported γ secretase inhibitor (MDL 28170) for 1 h, followed by washing to remove radiolabel and MDL 28170. The media is replaced and test compounds are added. The cells are chased for increasing periods of times and Aβ is isolated from the conditioned medium and C-terminal fragments from cell lysates (see above). The test compound is characterized whether a stabilization of C-terminal fragments is observed and whether Aβ is generated from these accumulated precursor. A typical test compound prevents the generation of Aβ out of accumulated C-terminal fragments and is considered active with an $IC_{50}$ less than 100 µM.

Dosage and Formulation

The compound of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compound of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compound of this invention can be administered by any means that produces contact of the active agent with the agent's site of action in the body of a host, such as a human or a mammal. The compound can be administered by any conventional means available for use in conjunction with pharmaceuticals, either as individual therapeutic agents or in a combination of therapeutic agents. The compound can be administered alone, but generally administered with a pharmaceutical carrier selected on the basis of the chosen route of administration and standard pharmaceutical practice.

The dosage regimen for the compound of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, the compounds of the present invention may be administered in a single daily dose, or the total daily dosage may be administered in divided doses of two, three, or four times daily.

The compound for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compound herein described in detail can form the active ingredient, and is typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compound of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compound of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I),

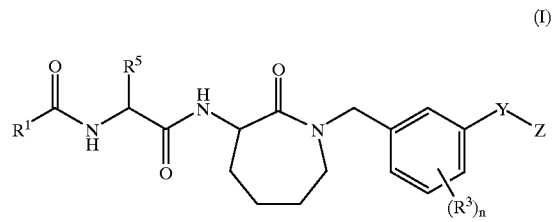

(I)

or a pharmaceutically acceptable salt thereof, wherein:

$R^1$ is $C_1$–$C_6$ alkyl substituted with 0–3 $R^{1a}$; $C_6$–$C_{10}$ aryl substituted with 0–3 $R^{1b}$; $C_3$–$C_6$ cycloalkyl substituted with 0–3 $R^{1b}$; or 5 to 10 membered heterocycle substituted with 0–3 $R^{1b}$; wherein said hetereocycle is saturated, partially unsaturated, or unsaturated; said hetereocycle is monocyclic or bicyclic; and said hetereocycle consists of carbon atoms and 1, 2, 3 or 4 heteroatoms independently selected from the group consisting of N, O and S;

$R^{1a}$, at each occurrence, is independently selected from: H, $CF_3$, $OR^{14}$, Cl, F, Br, I, =O, CN, $NO_2$, $NR^{15}R^{16}$; $C_3$–$C_{10}$ carbocycle substituted with 0–3 $R^{1b}$; $C_6$–$C_{10}$ aryl substituted with 0–3 $R^{1b}$; and 5 to 10 membered heterocycle substituted with 0–3 $R^{1b}$; wherein said heterocycle is saturated, partially unsaturated, or unsaturated; said hetereocycle is monocyclic or bicyclic; and said hetereocycle consists of carbon atoms and 1, 2, 3 or 4 heteroatoms independently selected from the group consisting of N, O and S;

$R^{1b}$, at each occurrence, is independently selected from H, OH, $C_1$–$C_4$ alkyl, $C_1$–$C_4$ alkoxy, Cl, F, Br, I, CN, $N_3$, $NO_2$, $NR^{15}R^{16}$, phenoxy, $C_1$–$C_4$ thioalkoxy and $CF_3$;

$R^5$ is $C_1$–$C_4$ alkyl, cyclopropyl, cyclopropylmethyl, cyclopropylethyl, cyclobutyl, cyclobutylmethyl, or cyclobutylethyl;

$R^3$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

n is 0, 1, 2, or 3;

Y is a bond, —C(=O), —O—, —S—, —N($R^{19}$)—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;

Z is $C_1$–$C_3$ alkyl substituted with 0–2 $R^{12}$; $C_6$–$C_{10}$ aryl substituted with 0–4 $R^{12b}$; $C_3$–$C_{10}$ carbocycle substituted with 0–2 $R^{12}$; or 5 to 10 membered heterocycle substituted with 0–4 $R^{12b}$; wherein said hetereocycle is saturated, partially unsaturated, or unsaturated; said hetereocycle is monocyclic or bicyclic; and said hetereocycle consists of carbon atoms and 1, 2, 3 or 4 heteroatoms independently selected from the group consisting of N, O and S;

$R^{12}$ is $C_6$–$C_{10}$ aryl substituted with 0–4 $R^{12b}$; or $C_3$–$C_{10}$ carbocycle substituted with 0–2 $R^{12}$;

$R^{12b}$, at each occurrence, is independently selected from H, OH, $C_1$–$C_6$ alkyl, $C_1$–$C_6$ thioalkyl, $C_1$–$C_4$ alkoxy, $C_1$–$C_4$ haloalkoxy, $C_1$–$C_4$ haloalkyl, Cl, F, Br, I, CN, $NO_2$, $NR^{15}R^{16}$, and $CF_3$;

$R^{14}$ is H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, benzyl, phenethyl, —C(=O)—($C_1$–$C_6$ alkyl) and —S(=O)$_2$—($C_1$–$C_6$ alkyl);

$R^{19}$, at each occurrence, is independently selected from H, OH, $C_1$–$C_6$ alkyl, phenyl, benzyl, phenethyl, —C(=O)—($C_1$–$C_6$ alkyl), and —S(=O)$_2$—($C_1$–$C_6$ alkyl); and $R^{19b}$ is H, $C_1$–$C_6$ alkyl, $C_3$–$C_8$ cycloalkyl, phenyl, benzyl or phenethyl.

2. A compound of claim 1 of Formula (I),

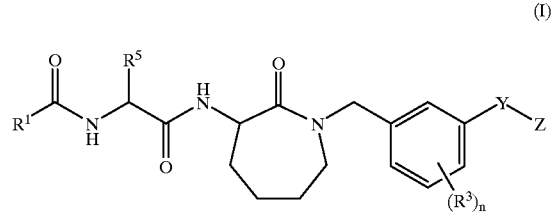

(I)

or a pharmaceutically acceptable salt thereof, wherein:

$R^1$ is $C_1$–$C_6$ alkyl substituted with 0–1 $R^{1a}$; $C_3$–$C_6$ cycloalkyl substituted with 0–1 $R^{1b}$; phenyl substituted with 0–2 $R^{1b}$; naphthyl substituted with 0–2 $R^{1b}$; or pyridyl substituted with 0–2 $R^{1b}$;

$R^{1a}$, at each occurrence, is independently selected from: H, $CF_3$, $OR^{14}$, Cl, F, Br, I; $C_3$–$C_{10}$ carbocycle substituted with 0–3 $R^{1b}$; and $C_6$–$C_{10}$ aryl substituted with 0–3 $R^{1b}$;

$R^{1b}$, at each occurrence, is independently selected from H, OH, methyl, ethyl, propyl, butyl, methoxy, ethoxy, propoxy, butoxy, Cl, F, Br, I, CN, $NO_2$, $N_3$, $SCH_3$, $NR^{15}R^{16}$, phenoxy, and $CF_3$;

$R^5$ is methyl, ethyl, propyl, isopropyl, butyl, isobutyl, cyclopropylmethyl, or cyclobutylmethyl;

$R^3$, at each occurrence, is independently selected from H, OH, methyl, ethyl, propyl, butyl, methoxy, ethoxy, propoxy, butoxy, Cl, F, Br, I, CN, $NO_2$, and $CF_3$;

n is 0, 1, or 2;

Y is a bond, —C(=O)—, —O—, —S—, —C(=O)O—, or —OC(=O)—;

Z is $C_1$–$C_3$ alkyl substituted with 0–2 $R^{12}$; or $C_6$–$C_{10}$ aryl substituted with 0–4 $R^{12b}$;

$R^{12}$ is $C_6$–$C_{10}$ aryl substituted with 0–4 $R^{12b}$; or $C_3$–$C_6$ carbocycle substituted with 0–4 $R^{12b}$;

$R^{12b}$, at each occurrence, is independently selected from H, OH, $C_1$–$C_4$ alkyl, $C_1$–$C_4$ alkoxy, Cl, F, Br, I, CN, $NO_2$, $SCH_3$, $NR^{15}R^{16}$, and $CF_3$;

$R^{14}$ is H, phenyl, benzyl, or $C_1$–$C_6$ alkyl;

$R^{15}$, at each occurrence, is independently selected from H, $C_1$–$C_4$ alkyl, benzyl, and phenethyl; and $R^{16}$, at each occurrence, is independently selected from H, $C_1$–$C_4$ alkyl, benzyl, and phenethyl.

3. A compound of claim 2 of Formula (I),

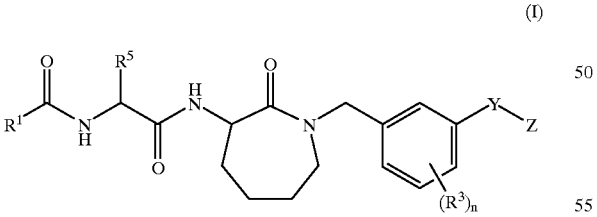

(I)

or a pharmaceutically acceptable salt thereof, wherein:

$R^1$ is methyl, ethyl, propyl, butyl, pentyl, hexyl, cyclopropyl, cyclobutyl, cyclopentyl, cyclohexyl, naphthyl, pyridyl; methyl substituted with 1 $R^{1a}$; ethyl substituted with 1 $R^{1a}$; or phenyl substituted with 1–3 $R^{1b}$;

$R^{1a}$, at each occurrence, is independently selected from: H, $CF_3$, $OR^{14}$, Cl, F, Br, I; $C_3$–$C_6$ cycloalkyl substituted with 0–3 $R^{1b}$; and phenyl substituted with 0–3 $R^{1b}$;

$R^{1b}$, at each occurrence, is independently selected from H, OH, methyl, ethyl, propyl, butyl, methoxy, ethoxy, propoxy, butoxy, Cl, F, Br, I, CN, $NO_2$, $N_3$, $SCH_3$, $NR^{15}R^{16}$, phenoxy, and $CF_3$;

$R^5$ is methyl;

$R^3$, at each occurrence, is independently selected from H, OH, methyl, ethyl, methoxy, ethoxy, Cl, F, Br, I, CN, $NO_2$, and $CF_3$;

n is 0 or 1;

Y is a bond or —O—;

Z is $C_1$–$C_3$ alkyl substituted with 0–2 $R^{12}$; or phenyl substituted with 0–3 $R^{12b}$;

$R^{12}$ is $C_3$–$C_6$ cycloalkyl substituted with 0–3 $R^{12b}$; phenyl substituted with 0–3 $R^{12b}$;

$R^{12b}$, at each occurrence, is independently selected from H, OH, methyl, ethyl, propyl, butyl, methoxy, ethoxy, propoxy, butoxy, $SCH_3$, $C_1$–$C_2$ haloalkyl, $C_1$–$C_2$ haloalkoxy, Cl, F, Br, I, CN, $NO_2$, $NR^{15}R^{16}$, and $CF_3$;

$R^{14}$ is H, methyl, ethyl, phenyl, or benzyl;

$R^{15}$, at each occurrence, is independently selected from H, methyl, ethyl, propyl, butyl, benzyl, and phenethyl;

R[16], at each occurrence, is independently selected from H, methyl, ethyl, propyl, butyl, benzyl, and phenethyl.

4. A compound of claim 3 of Formula (Ia),

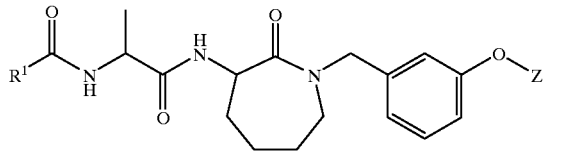

(Ia)

or a pharmaceutically acceptable salt thereof, wherein:

R[1] is methyl, ethyl, propyl, butyl, pentyl, hexyl, cyclopropyl, cyclobutyl, cyclopentyl, cyclohexyl, naphthyl, pyridyl; methyl substituted with 1 $R^{1a}$; ethyl substituted with 1 $R^{1a}$; or phenyl substituted with 1–3 $R^{1b}$;

$R^{1a}$ is phenyl substituted with 0–3 $R^{1b}$; cyclopropyl substituted with 0–1 $R^{1b}$; cyclobutyl substituted with 0–1 $R^{1b}$; cyclopentyl substituted with 0–1 $R^{1b}$; or cyclohexyl substituted with 0–1 $R^{1b}$;

$R^{1b}$, at each occurrence, is independently selected from H, OH, methyl, ethyl, propyl, butyl, methoxy, ethoxy, propoxy, butoxy, Cl, F, Br, I, CN, $NO_2$, $N_3$, $SCH_3$, phenoxy, and $CF_3$;

Z is methyl substituted with $R^{12}$; or phenyl substituted with 0–2 $R^{12b}$;

$R^{12}$ is phenyl substituted with 0–2 $R^{12b}$;

$R^{12b}$, at each occurrence, is independently selected from H, OH, methyl, ethyl, methoxy, ethoxy, Cl, F, Br, I, CN, $NO_2$, $SCH_3$, $NR^{15}R^{16}$, $OCF_3$, and $CF_3$;

R[15], at each occurrence, is independently selected from H, methyl, and ethyl; and R[16], at each occurrence, is independently selected from H, methyl, and ethyl.

5. A compound of claim 4 of Formula (Ib):

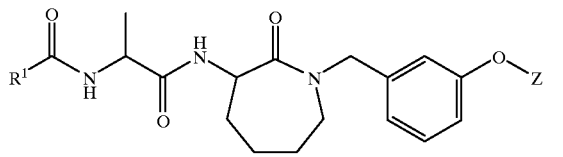

(Ib)

or a pharmaceutically acceptable salt thereof, wherein:

R[1] is methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, —CH₂-cyclopropyl, —CH₂-cyclobutyl, —CH₂-cyclohexyl, —CH₂-cyclopentyl, —CH₂CH₂-cyclopropyl, —CH₂CH₂-cyclobutyl, —CH₂CH₂-cyclohexyl, —CH₂CH₂cyclopentyl, phenylmethyl, 2-chlorophenylmethyl, 2-fluorophenylmethyl, 2-bromophenylmethyl, 2-hydroxyphenylmethyl, 2-nitrophenylmethyl, 2-methylphenylmethyl, 2-methoxyphenylmethyl, 2-phenoxyphenylmethyl, 2-trifluoromethylphenylmethyl, 3-hydroxyphenylmethyl, 3-nitrophenylmethyl, 3-fluorophenylmethyl, 3-chlorophenylmethyl, 3-bromophenylmethyl, 3-thiomethoxyphenylmethyl, 3-methylphenylmethyl, 3-trifluoromethylphenylmethyl, 3-methoxyphenylmethyl, 4-chlorophenylmethyl, 4-bromophenylmethyl, 4-nitrophenylmethyl, 4-methylphenylmethyl, 4-hydroxyphenylmethyl, 4-methoxyphenylmethyl, 4-ethoxyphenylmethyl, 4-butoxyphenylmethyl, 4-isopropylphenylmethyl, 4-trifluoromethylphenylmethyl, 4-azidophenylmethyl, 4-cyanophenylmethyl,4-ethylphenylmethyl, 4-fluorophenylmethyl, 4-iodophenylmethyl, 2,3-dichlorophenylmethyl, 2,5-difluorophenyl, 2,3-difluorophenylmethyl, 2,4-dichlorophenylmethyl, 2,5-dimethoxyphenylmethyl, 3,4-dichlorophenylmethyl, 3,4-difluorophenylmethyl, 3,4-dimethoxyphenylmethyl, 3,5-difluorophenylmethyl, 3,5-dichlorophenylmethyl, 3,5-di-(trifluoromethyl)phenylmethyl, 3,5-dimethoxyphenylmethyl, 2,4-difluorophenylmethyl, 2,6-difluorophenylmethyl, 2,5-difluorophenylmethyl, 2-fluoro-3-trifluoroethylphenylmethyl, 4-fluoro-2-trifluoromethylphenylmethyl, 2-fluoro-4-trifluoromethyl-phenylmethyl, 2-choro-6-fluorophenylmethyl, 2-fluoro-6-chlorophenylmethyl, 2,5-dimethylphenylmethyl, 2-fluoro-3-trifluoromethylphenylmethyl, 3-(trifluoromethyl)—4-chloro-phenylmethyl, 3-chloro-4-cyano-phenylmethyl, 3-chloro-4-iodo-phenylmethyl, 3,4,5-trichlorophenylmethyl, 3,4,5-trifluorophenylmethyl, 3,4,5-trimethoxyphenylmethyl, 3,4,5-tri(trifluoromethyl)phenylmethyl, 2,4,6-trifluorophenylmethyl, 2,4,6-trimethylphenylmethyl, 2,4,6-tri(trifluoromethyl)phenylmethyl, 2,3,5-trifluorophenylmethyl, 2,4,5-trifluorophenylmethyl, 2-phenylethyl, 2-(4-nitrophenyl)ethyl, 2-(4-methoxyphenyl)ethyl, (1-phenyl)ethyl, 1-(p-chorophenyl)ethyl, (1-trifluoromethyl)phenylethyl, (4-methoxyphenyl)ethyl, 1-naphthyl, 2-naphthyl, pyrid-2-yl, pyrid-3-yl, or pyrid-4-yl; and Z is is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, or 4-CF₃O-phenyl.

6. A compound according to claim 5 of Formula:

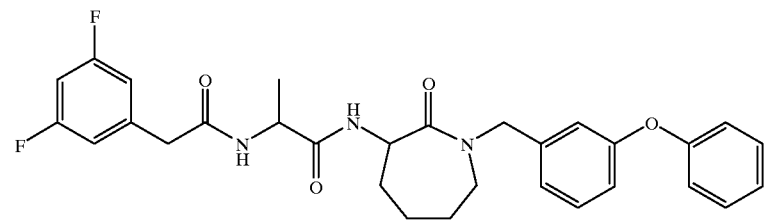

or a pharmaceutically acceptable salt thereof.

7. A pharmaceutical composition comprising a compound of claim 1 and a pharmaceutically acceptable carrier.

8. A pharmaceutical composition comprising a compound of claim 2 and a pharmaceutically acceptable carrier.

9. A pharmaceutical composition comprising a compound of claim 3 and a pharmaceutically acceptable carrier.

10. A pharmaceutical composition comprising a compound of claim 4 and a pharmaceutically acceptable carrier.

11. A pharmaceutical composition comprising a compound of claim 5 and a pharmaceutically acceptable carrier.

12. A pharmaceutical composition comprising a compound of claim 6 and a pharmaceutically acceptable carrier.

13. A method for the treatment of Alzheimer's Disease comprising administering to a host in need of such treatment a therapeutically effective amount of a compound of claim 1.

14. A method for the treatment of Alzheimer's Disease comprising administering to a host in need of such treatment a therapeutically effective amount of a compound of claim 2.

15. A method for the treatment of Alzheimer's Disease comprising administering to a host in need of such treatment a therapeutically effective amount of a compound of claim 3.

16. A method for the treatment of Alzheimer's Disease comprising administering to a host in need of such treatment a therapeutically effective amount of a compound of claim 4.

17. A method for the treatment of Alzheimer's Disease comprising administering to a host in need of such treatment a therapeutically effective amount of a compound of claim 5.

18. A method for the treatment of Alzheimer's Disease comprising administering to a host in need of such treatment a therapeutically effective amount of a compound of claim 6.

* * * * *